United States Patent [19]
de Vries et al.

[11] Patent Number: 5,991,659
[45] Date of Patent: Nov. 23, 1999

[54] PACING SYSTEM WITH FULL RANGE SUDDEN RATE DROP DETECTION AND RESPONSIVE PACING INTERVENTION

[75] Inventors: Bernhard de Vries, Dieren; Hendrik Reineman, Zutphen; Johannes G. F. Idink, Arnhem; Hendrik van Rooijen, Nijkerk, all of Netherlands

[73] Assignee: Vitatron Medical, B.V., Dieren, Netherlands

[21] Appl. No.: 09/164,012

[22] Filed: Sep. 30, 1998

[51] Int. Cl.⁶ .................................................. A61N 1/368
[52] U.S. Cl. .................................................. 607/9
[58] Field of Search ..................... 607/9, 17, 4

[56] References Cited

U.S. PATENT DOCUMENTS

| | | | |
|---|---|---|---|
| 3,921,642 | 11/1975 | Preston | 128/419 PG |
| 4,030,510 | 6/1977 | Bowers | 607/9 |
| 4,363,325 | 12/1982 | Roline et al. | 607/9 |
| 5,016,630 | 5/1991 | Moberg | 128/419 PG |
| 5,247,930 | 9/1993 | Begemann et al. | 607/11 |
| 5,282,465 | 2/1994 | van der Veen et al. | 607/17 |
| 5,284,491 | 2/1994 | Sutton et al. | 607/17 |
| 5,441,525 | 8/1995 | Shelton et al. | 607/23 |
| 5,501,701 | 3/1996 | Markowitz et al. | 607/9 |
| 5,531,771 | 7/1996 | van der Veen | 607/9 |
| 5,540,728 | 7/1996 | Shelton et al. | 607/23 |
| 5,676,686 | 10/1997 | Jensen et al. | 607/9 |
| 5,725,561 | 3/1998 | Stroebel et al. | 607/9 |
| 5,782,886 | 7/1998 | Kuiper et al. | 607/17 |

*Primary Examiner*—Kennedy J. Schaetzle
*Attorney, Agent, or Firm*—Thomas F. Woods; Harold Patton; Michael J. Jaro

[57] ABSTRACT

There is provided a pacemaker system with an SRD detection and intervention feature, which enables a simple way of initiating confirmation of SRD, i.e., looking for an AS/AP transition in a DDD or DDI pacemaker, or a transition from a VS to a VP in a DDI pacemaker. This simple initiation of SRD confirmation is made possible by use of a relatively wide hysteresis band which is normally operative when a spontaneous rate is present, and which tracks physiological changes in the patient's natural rate, across the pacemaker rate range. Transitions which result from a gradual decrease in natural rate and thus represent physiological bradycardia are not interpreted as suggesting SRD. The detection is confirmed only after a predetermined number of pace pulses are delivered at the hysteresis rate, i.e., 1–5 pulses. In a preferred embodiment, after confirmation of SRD, pacing starts at a programmable intervention rate, and rate flywheels downward toward a lower rate limit, with intermittent hysteresis scans at a lower rate to enable recovery of an underlying natural rate. The SRD mode is left whenever recovery of a natural rate is confirmed, as by sensing a predetermined number of consecutive natural atrial beats in DDD mode or atrial and/or ventricular beats in DDI mode.

22 Claims, 11 Drawing Sheets

PACING SYSTEM WITH FULL RANGE SUDDEN RATE DROP DETECTION AND RESPONSIVE PACING INTERVENTION

FIELD OF THE INVENTION

This invention lies in the field of cardiac pacing systems and methods and, in particular, dual chamber pacing systems that have the capacity to detect a sudden drop in the patient's spontaneous heart rate and to respond to such a sudden drop with a special pacing routine.

BACKGROUND OF THE INVENTION

It is well known that certain patients experience loss of consciousness due to a sudden drop in blood pressure and/or heart rate. In many patients with such a cardioinhibitory component, intervention by pacing may help delay or reduce symptoms. The indicated forms of pacing to provide such help are DDD and DDD(R) pacing (hereinafter both referred to as DDD), where AV synchrony is maintained as such as possible; or DDI or DDI(R), or AV sequential pacing (hereinafter both referred to as DDI). In today's programmable pacemakers, there are provided algorithms for detecting sudden rate drop, but they generally are of limited use, and do not reliably detect sudden rate drop over the full range of physiological rates that a patient may experience. Such prior art solutions have generally been based on obtaining a sample of the patient's ongoing intrinsic rate history, and may incorporate some form of rate hysteresis to minimize the occasions when the pacemaker needs to override the intrinsic rate with delivered pace pulses.

The feature of rate hysteresis is well known in cardiac pacemakers. For example, many single chamber VVI pacemakers provide a form of rate hysteresis which is designed to prolong the next pacing escape interval which is set after a spontaneous, or natural ventricular beat. For example, the pacemaker may be programmed to pace at 70 beats per minute (bpm), but as long as natural beats are being sensed at rates above 70 bpm, the escape interval may be set to correspond to a somewhat lower rate, e.g., 60–65 bpm. The advantage of such hysteresis is that it enables the pacemaker to follow a mildly lower natural rhythm, i.e., one which might be just slightly below the lower rate limit (LRL) which has been programmed for pacing but still at a high enough rate that it is not necessary to override these natural beats with pacing. This achieves the advantages of maintaining the heart's AV synchrony as much as possible, and extending pacemaker longevity due to not delivering as many pace pulses. In dual chamber pacemakers, e.g. a DDD pacemaker where maximizing AV synchrony is an aim, providing hysteresis with respect to the atrial sensing enables increased tracking of natural atrial beats. Even in a DDI pacemaker, which does not track natural atrial beats as such, it remains desirable to maximize the number of atrial sense-ventricular sense (AS-VS) cycles, so as to maximize cardiac cycles where the heart is permitted to beat with its natural AV synchrony.

A known problem with hysteresis in cardiac pacing systems is that it can lead to excessive changes in rate. Usually a hysteresis rate is set which does not take into account the rate of the natural beats just prior to a sudden rate drop. With conventional hysteresis, whether the prior natural rate is close to the lower rate limit or far exceeds it, whenever the natural rate drops below the hysteresis rate, the pacemaker delivers a pace pulse at a rate corresponding to the hysteresis rate. Thus, a normal rate of 80–85 bpm could be followed by a pace pulse coming at an interval corresponding to a rate of only 60. Such a large drop in heart rate can have possible hemodynamic consequences, and the patient may experience a palpitation because of the sudden change. Further, in most hysteresis schemes, the pacing rate then goes to the pacing limit that had been set prior to losing the natural rate, and is maintained at such rate limit until a natural rate above this limit spontaneously reappears. This can mask the existence of an underlying natural rate just below the pacing limit, and aggravate the overall effect of loss of AV synchrony. It is thus seen that pacemaker performance would be improved by correlating the hysteresis function to the prior natural rate, and by improving the opportunity to recapture any underlying natural rate after pacing has taken over. There have been a number of different arrangements designed to enhance the hysteresis feature in cardiac pacemakers. See, for example, U.S. Pat. No. 5,016,630, which discloses a rate responsive pacemaker that varies the pacing rate, and provides a hysteresis interval which varies as a function of the escape interval corresponding to the dynamic pacing rate. It is also known to use the rate of change in the spontaneous intervals before hysteresis pacing to vary the escape interval after loss of the natural rate and takeover of hysteresis pacing. See U.S. Pat. Nos. 5,284,491 and 5,782,886. See also U.S. Pat. No. 3,921,642, which describes hysteresis "searching" for an underlying natural beat.

However, what remains needed in the art is a pacing system which optimizes hysteresis so as to detect a sudden rate drop anywhere across the rate spectrum, i.e., from the upper pacing limit to the lower pacing limit; and to respond to a detected sudden rate drop (SRD) with a pacing modality that gradually takes pacing rate to a safe rate while optimizing the opportunity to find an underlying natural rate and restore AV synchrony as quickly as possible. It is important to provide both reliable detection of SRD, and an optimized response to restore intrinsic physiological heart beats.

SUMMARY OF THE INVENTION

It is an object of this invention to provide a pacing system with an improved manner of detecting sudden rate drop from a natural rate at any point in the pacemaker rate range, and an improved manner of responding to such a sudden rate drop, so as to maximize intrinsic AV synchrony in a dual chamber pacemaker.

The above object is provided in a dual chamber pacemaker which provides a physiological rate which continuously tracks the natural atrial rate when one is present; a hysteresis rate which tracks the physiological rate more slowly and thus provides for a hysteresis takeover rate which varies with the natural atrial rate; detection logic for determining when the natural rate has dropped below the hysteresis rate and a predetermined number of pace pulses have followed; and an SRD pacing modality which intervenes following a detected sudden rate drop to take the atrial pacing rate from a programmed intervention rate down toward a predetermined lower pacing limit, combined with periodic atrial hysteresis searching until the lower limit is reached.

In a preferred embodiment, the pacemaker continuously calculates a phys_rate, which substantially tracks the natural atrial rate except for quick changes, and which moves toward the pacing rate when there is no atrial rate which can be tracked. A dynamic pacing rate (DPL) tracks at a given number (e.g., 0 to 2.5) of ppm below phys_rate; and an atrial hysteresis rate tracks at a given ms band below DPL. Sudden rate drop is detected when the natural rate drops through the hysteresis band and there is no atrial sense after n, (e.g., 1–5) detection paces at the hysteresis rate. Following detection, the pacemaker goes into an intervention mode; phys_rate and DPL are set at a programmed intervention rate, and pacing is done at the DPL rate, with a slow flywheel deceleration toward the programmed lower rate limit. The intervention is also preferably characterized by a recovery search, where an atrial hysteresis is forced every $n_2$ pace pulses, e.g., pacing rate is dropped from the DPL rate by a programmable hysteresis amount. If at any time during intervention the spontaneous rate reappears, during a hysteresis search or otherwise, and stays for 1 or more consecutive cycles, the pacing rate (DPL) decelerates normally, and the pacemaker returns to normal situation handling.

In a situation where the spontaneous rate, and thus the phys_rate, drops smoothly through a programmed detection off rate, the pacemaker logic does not determine that there has been a sudden rate drop, i.e., it discriminates between a physiological bradycardia and a pathological rate drop. In this situation, pacing clamps at the lower rate limit, and the pacemaker is put into an "unknown situation" state for further handling.

DESCRIPTION OF THE PREFERRED EMBODIMENTS

Figure 1:
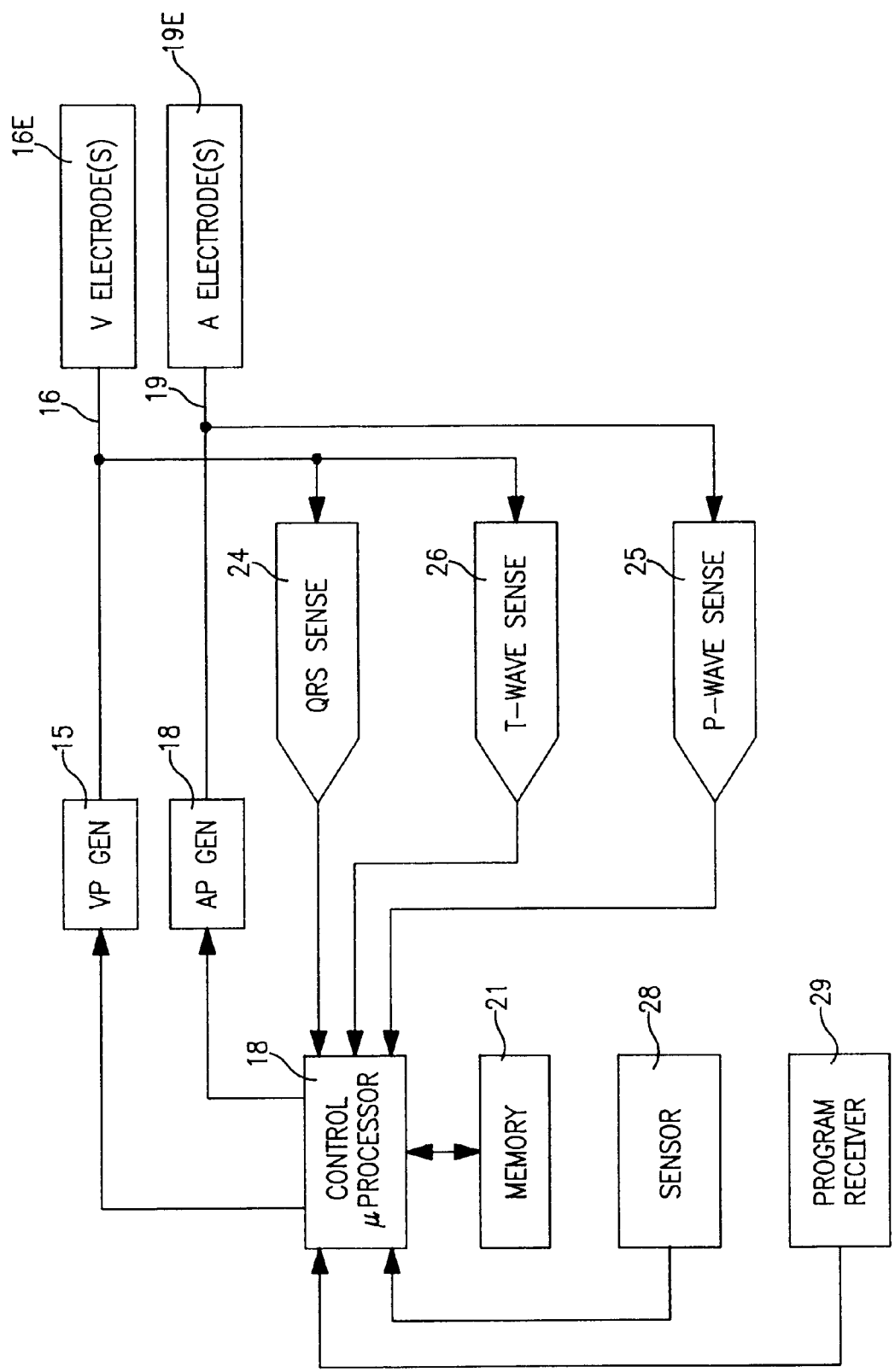
FIG. 1 is a block diagram of an embodiment of an overall pacing system according to this invention.

Referring now to FIG. 1, there is shown a block diagram of the primary functional components of an illustrative pacemaker system for use in this invention. A VP generator 15 provides pacing pulses, generated under control of block 20, for delivery through lead 16 to one or more ventricular electrodes 16E located in the patient's right ventricle. Likewise, AP generator 18 provides atrial pacing pulses, also generated under control of block 20, for delivery through lead 19 to one or more atrial electrodes 19E located in the patient's right atrium. While not shown, it is understood that the invention is further applicable to other multi-chamber configurations. Signals sensed by electrodes 16E are connected to QRS Sense circuit 24 which processed the signals and provides V-Sense, or VS signals to block 20. Signals from ventricular electrodes 16E are also passed to T-Wave sense circuit 26, which provides T-Sense signals to block 20, for use, e.g., in rate control based on the QT interval. Signals from atrial electrodes 19E are connected to P-Wave sense circuit 25, which outputs A-Sense, or AS signals to block 20. Block 20 controls the pacemaker functions, e.g., the cyclical functions of setting and timing out escape intervals; receiving sensed signals from the patient's heart and resetting escape intervals based on those signals; and carrying out special functions such as the SRD function of this invention. Block 20 preferably comprises a microprocessor and associated memory, shown at 21, for storing the required software routines.

The memory 21 suitably includes dedicated RAM and ROM. Control parameters and values can be programmed from an external programmer through program receiver 29, in a known manner. The pacemaker can be programmed to operate in different modes; this invention is illustrated in terms of a dual chamber pacemaker system operating in either the DDD/DDD(R) or DDI/DDI(R) mode. Sensor 28 may be used to provide a rate responsive parameter, e.g. activity, to be used alone or in combination with another parameter such as QT.

Figure 2A:
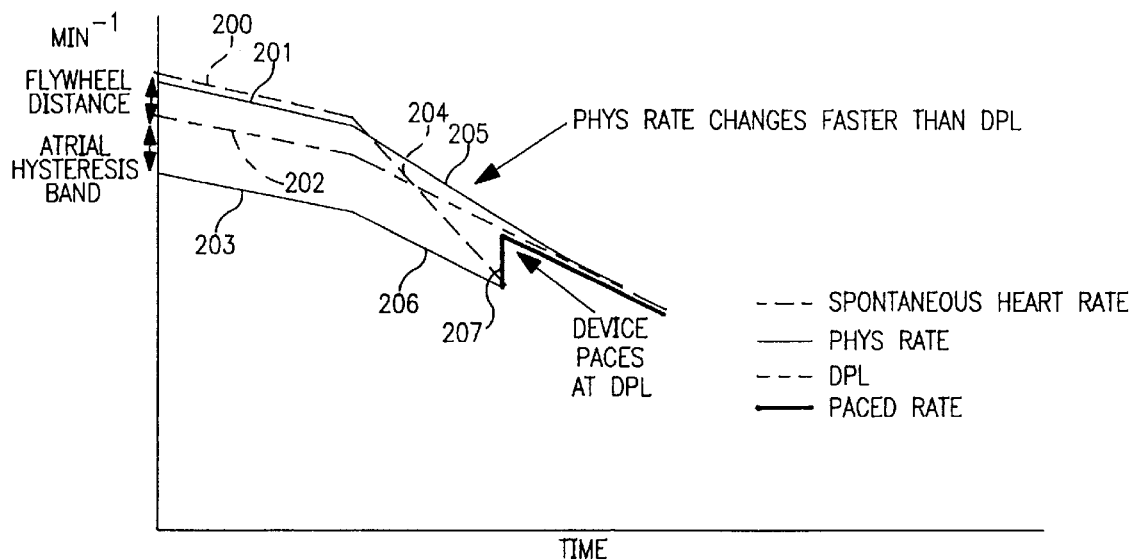
FIG. 2(a) is a decision rate diagram which illustrates a changing spontaneous heart rate, phys_rate, DPL, hysteresis rate and paced rate in a system without SRD intervention.

Referring now to FIGS. 2(a), (b) and (c), there are shown rate diagrams which provide background for an understanding of the SRD detection and intervention schemes of this invention. Reference is made to U.S. Pat. No. 5,247,930, incorporated by reference, for a disclosure of dynamic physiologic tracking based on decision rates which substantially track the spontaneous rate so long as it is present and physiological. FIG. 2(a) illustrates decision rates for normal behavior and a pacemaker without any SRD algorithm active. It shows flywheel and atrial hysteresis in terms of the spontaneous rate; the phys rate; the dynamic pacing limit (DPL); the atrial hysteresis rate; and the paced rate. Phys rate, which is disclosed in the reference U.S. Pat. No. 5,247,930, follows the spontaneous heart rate, with changes limited to, e.g., 2 bpm per cycle; without a spontaneous rate, Phys rate decreases slowly to the lower rate limit (LRL). As illustrated in FIG. 2(a), the spontaneous rate initially decreases slowly with time (200), and phys rate substantially follows it (201); DPL (202) follows Phys rate, at a flywheel distance (in bpm) below Phys rate, but change in DPL is more limited. An atrial hysteresis rate (203) is shown below DPL, at a predetermined band in ms below phys_rate. If atrial hysteresis is turned on, then the escape interval is extended by the hysteresis band after a physiological spontaneous atrial rate. The pacemaker will not start pacing if the spontaneous heart rate has reached DPL, but only after it has reached the extended escape interval, after which point it would start pacing at DPL. As seen in the drawing, when the spontaneous rate decelerates faster (204), the Phys rate follows, but at a slower rate (205); DPL and the hysteresis rate decrease more slowly than Phys rate (206). When the spontaneous rate reaches the bottom of the hysteresis band (207), pacing takes over at DPL, as shown.

Figure 2B:
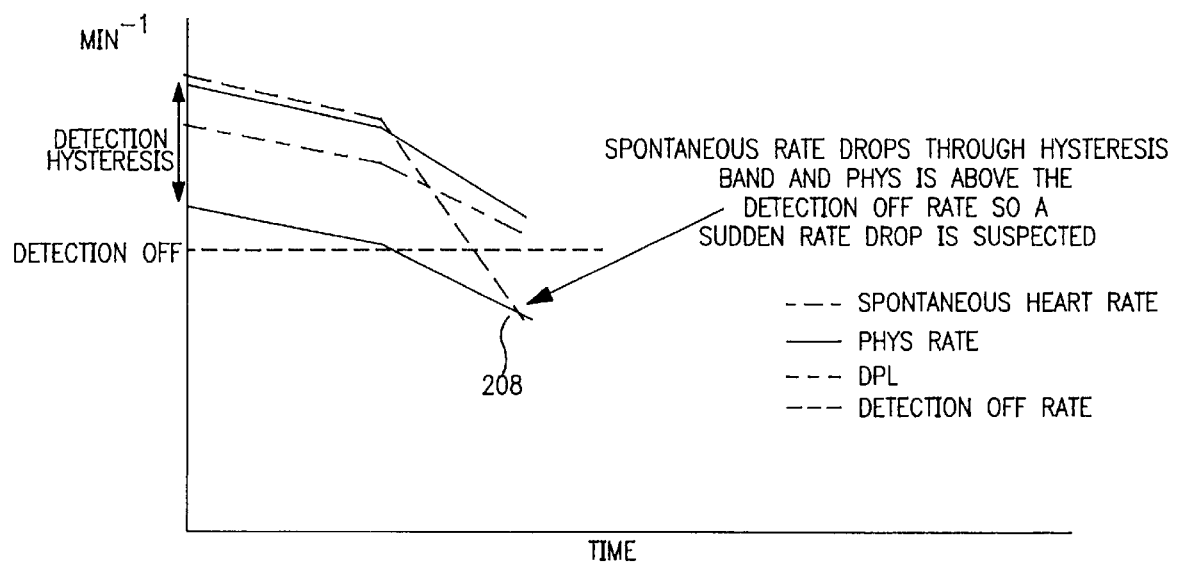
FIG. 2(b) is a rate diagram illustrating a normal sudden rate drop, where the detection off rate is not reached and the pacemaker logic concludes that there has been a sudden rate drop.

Referring now to FIG. 2(b), there is illustrated an example of a situation where there is a normal sudden rate drop, where a programmable rate identified as the Detection OFF rate is not reached by the Phys rate. Under normal situations, a large hysteresis band is used to check for a SRD. As shown, the detection hysteresis band is larger than the flywheel band; the flywheel band is preferably small, 2.5 ppm or less. A large hysteresis band is desired, and is programmed so that a normal heart rate fluctuation does not lead to SRD intervention. With this detection hysteresis in place, the difference between a normal fluctuation and a SRD can be determined as simply the difference between a sense and a pace, i.e., an AS/AP transition. In a DDD pacemaker, which aims to maximize AV synchrony, there may be more frequent problems than sudden rate drop, e.g., AV-block. Consequently, AV block is not a reason for determining SRD in a DDD system, and only an atrial pace can lead to SRD intervention. For a DDI pacemaker system, intervention can take place where either atrial rate or ventricular rate has dropped; this is anytime that AS-VS is not maintained, including occurrences of AV block. Thus, an AS/AP or a VS/VP transition can also indicate a suspected SRD in a DDI pacemaker. As used following, a "transition" means an AS/AP in DDD or DDI, or a VS/VP in DDI.

Figure 2C:
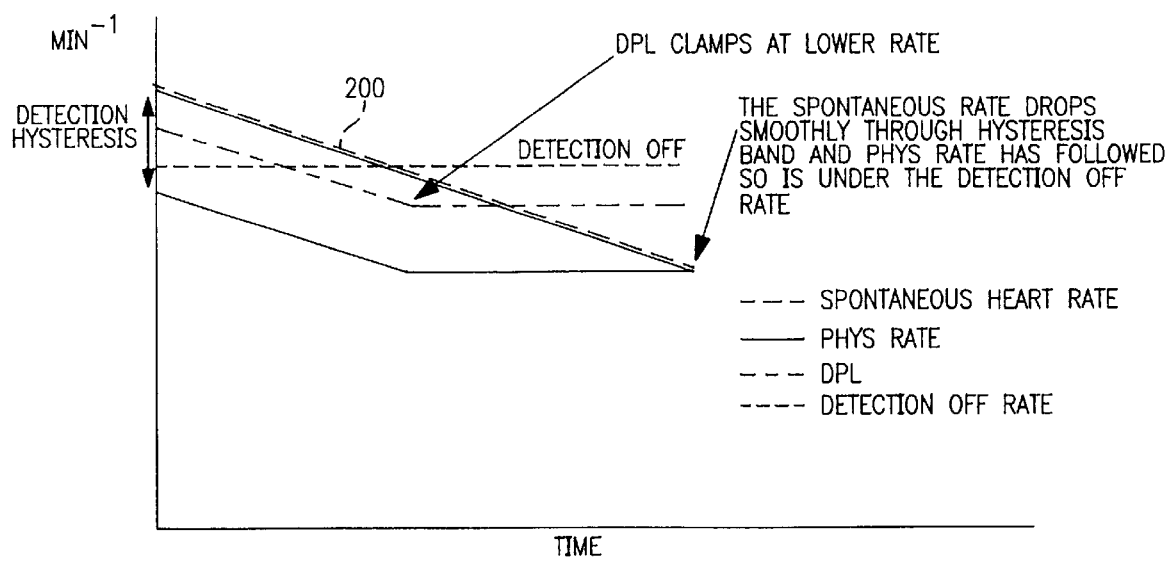
FIG. 2(c) is a rate diagram illustrating physiological bradycardia with rate drop through the detection off rate, where sudden rate drop cannot be concluded.

As seen in FIG. 2(b), the spontaneous rate drops through the hysteresis band (208), but the Phys rate remains above a programmed Detection OFF rate. This situation is interpreted as a pathological rate drop, and SRD is suspected. However, in the situation shown in FIG. 2(c), the spontaneous rate has dropped smoothly through the hysteresis band, and Phys rate has followed it so that it is under the Detection OFF rate when the spontaneous rate goes below the hysteresis band. The transition from AS to AP is not sufficient to suggest SRD, and this situation is interpreted as a physiological radycardia; the pacemaker will go into an "Unknown Situation" state, and react somewhat differently, as seen in FIG. 3(c).

Figure 3A:
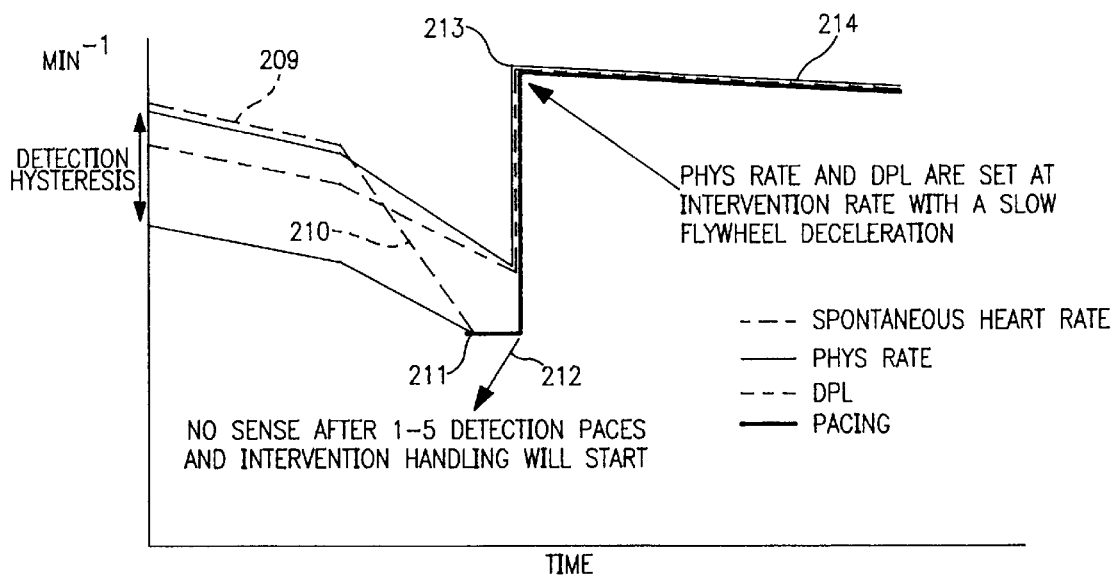
FIG. 3(a) is a rate diagram illustrating sudden rate drop intervention with slow flywheel deceleration from a programmed intervention rate.
Figure 3B:
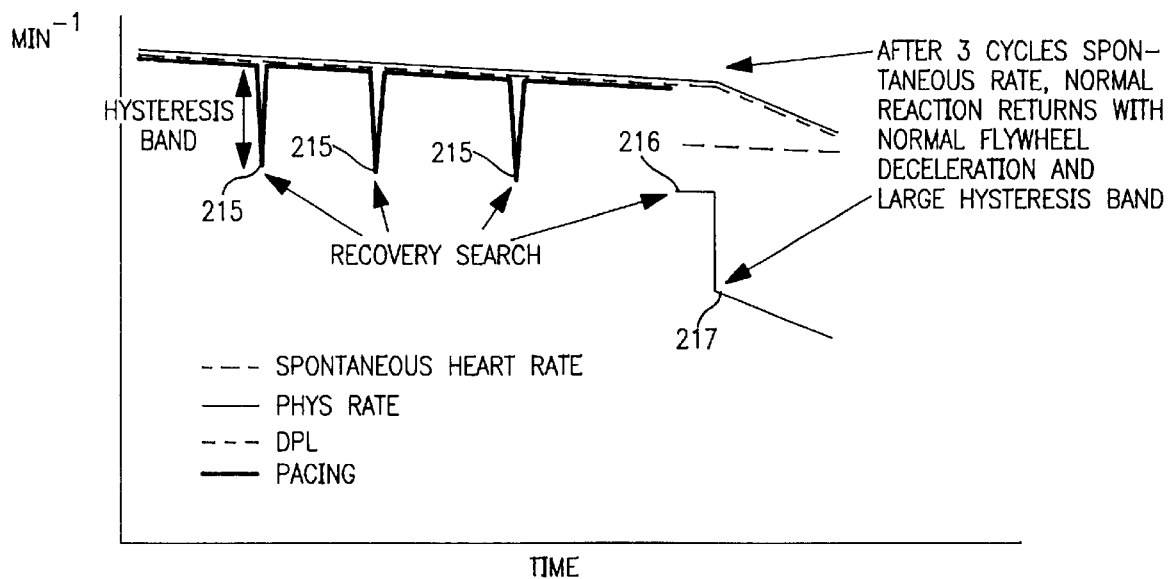
FIG. 3(b) is a rate diagram illustrating the inclusion of recovery hysteresis searching and a return to normal flywheel deceleration after a return of spontaneous beats.
Figure 3C:
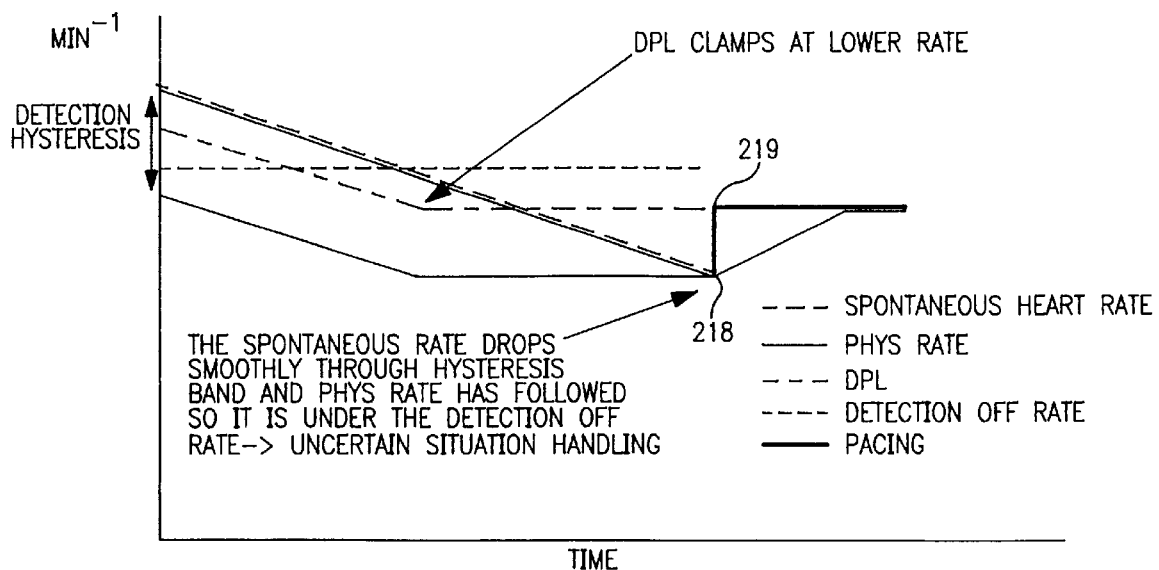
FIG. 3(c) is a rate diagram illustrating physiological bradycardia with rate drop through the hysteresis band which results in uncertain situation handling.

Referring now to FIG. 3(a), there is shown a rate diagram which depicts a situation where SRD is detected, and a first form of intervention pacing is provided. In the diagram, the spontaneous rate is shown initially decreasing relatively slowly with time (209), and then taking a steeper drop (210) to the point where the underlying rate is no longer sensed (211). At the point where the atrial hysteresis interval times out, there is an AS/AP transition; pacing is done at the rate corresponding to the bottom of the hysteresis band for a programmable number of cycles, e.g., 1–5 atrial paces (212). After this, there having been no intervening AS, the pacing rate is caused to step up to a programmable Intervention rate (213), and then slowly decreased with a flywheel deceleration (214). FIG. 3(b) illustrates a modified form of intervention pacing as programmed in a preferred embodiment, where periodic atrial hysteresis scans, or searches, are used to attempt to uncover an underlying spontaneous beat. As the pacing rate flywheels slowly down toward the LRL, every so many cycles, e.g., every 30–31 paces, an atrial hysteresis is forced (215), meaning that at least one AP is delivered after an escape interval which is extended by a hysteresis amount. In the situation illustrated, during the 4th search (216), an underlying spontaneous rate is found; after 3 cycles at this spontaneous rate (217), the pacemaker returns to a normal reaction, with normal flywheel deceleration of the DPL and a large hysteresis band. Alternatively, in the situation shown in FIG. 3(c), the Detection OFF rate is passed by phys_rate when the spontaneous rate drops through the hysteresis band (218), so the situation is handled as an Uncertain Situation, with pacing rate returning to the DPL (219) (which has been clamped at the lower rate limit) instead of to the Intervention rate. This situation is interpreted as a physiological bradycardia. Note that the DPL clamps at the programmed lower rate limit, and the hysteresis rate likewise is clamped at a lower limit. Accordingly, physiological bradycardia is indicated whenever the phys rate is below the programmable detection OFF rate, when a "transition" is detected.

Figure 4A:
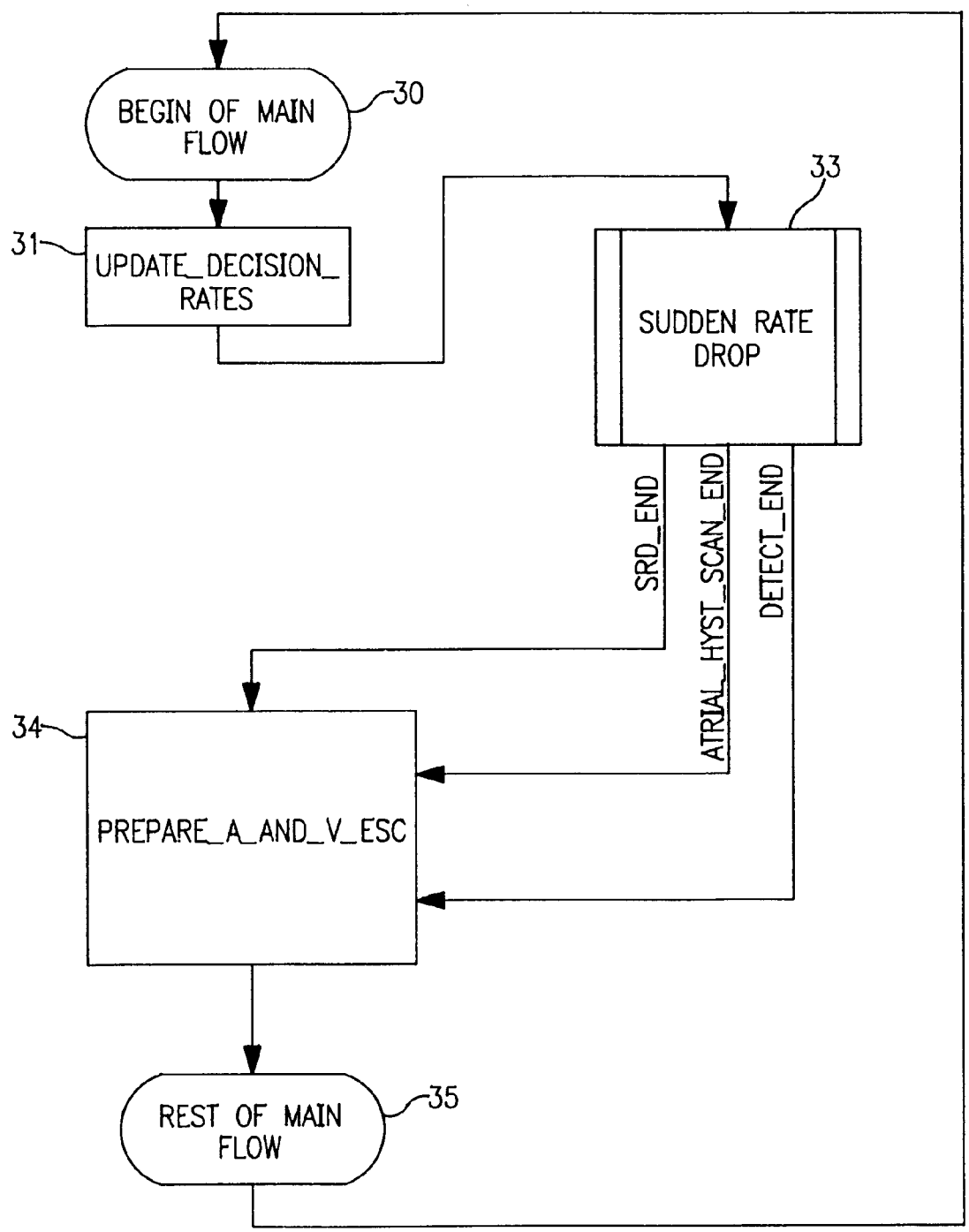
FIG. 4(a) is a flow diagram illustrating an overview of the place of a Sudden Rate Drop routine within the main handling routine, in accordance with this invention.

Referring now to FIG. 4(a), there is shown a block diagram showing the place of the SRD routine 33 within the overall Main Flow which is carried out cyclically. The main flow is entered at 30, and at 31 the Decision Rates are updated, based on Phys_rate. It is noted that this is the point where flywheel deceleration is executed, as is done during intervention following SRD detection. Then, the main flow proceeds to the SRD routine, shown at 33, and discussed in more detail below in connection with FIGS. 4(b), 5–9. As indicated, routine 33 can be exited in 3 different ways, and in each case the main flow next goes to block 34 and prepares the appropriate values of the escape intervals A_esc and V_esc. After this, the pacemaker carries out the rest of the main flow as indicated at 35, including atrial and ventricular event handling.

Figure 4B:
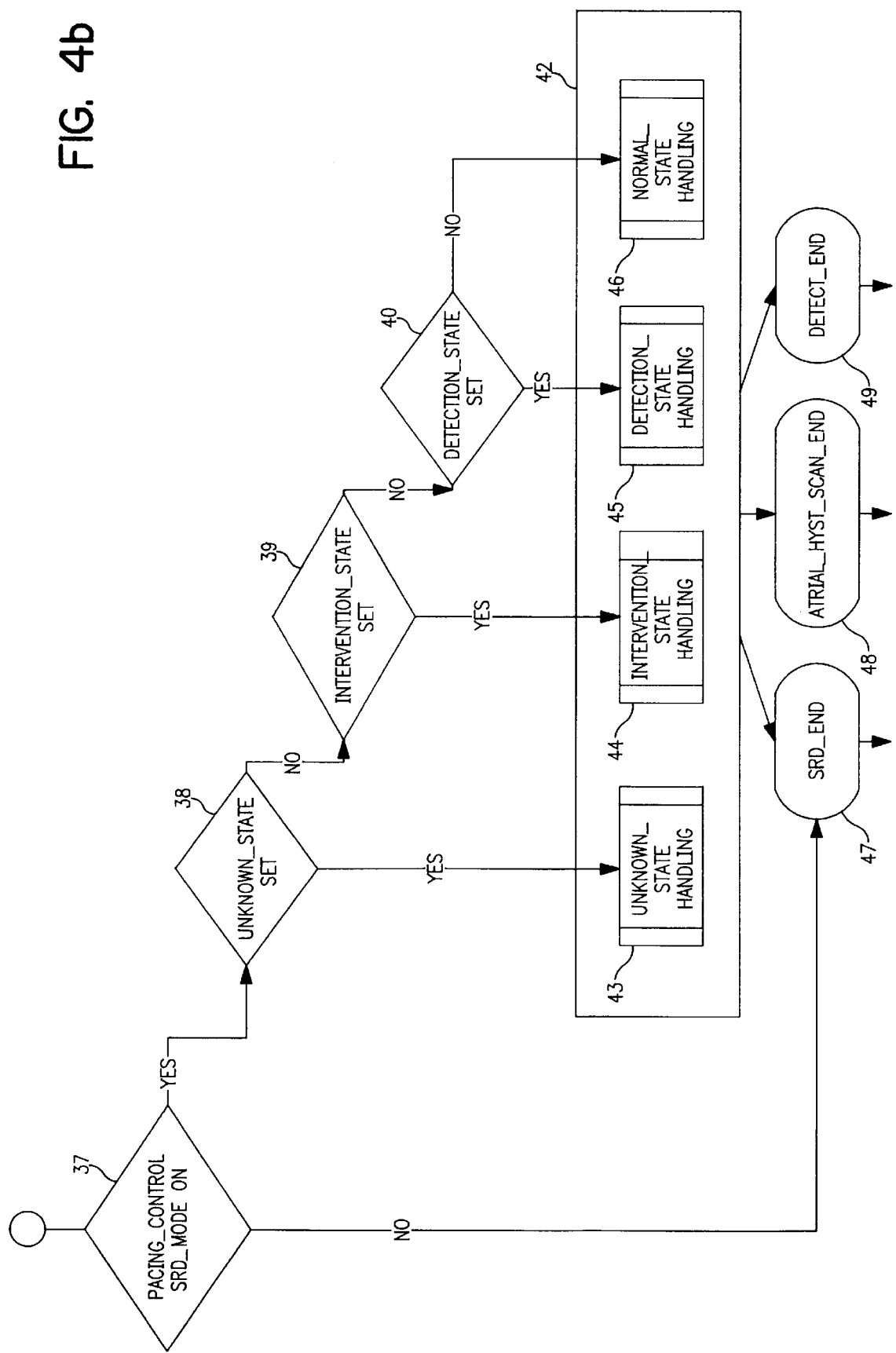
FIG. 4(b) is an overview flow diagram of a Sudden Rate Drop routine, illustrating the SRD states.
Figure 7:
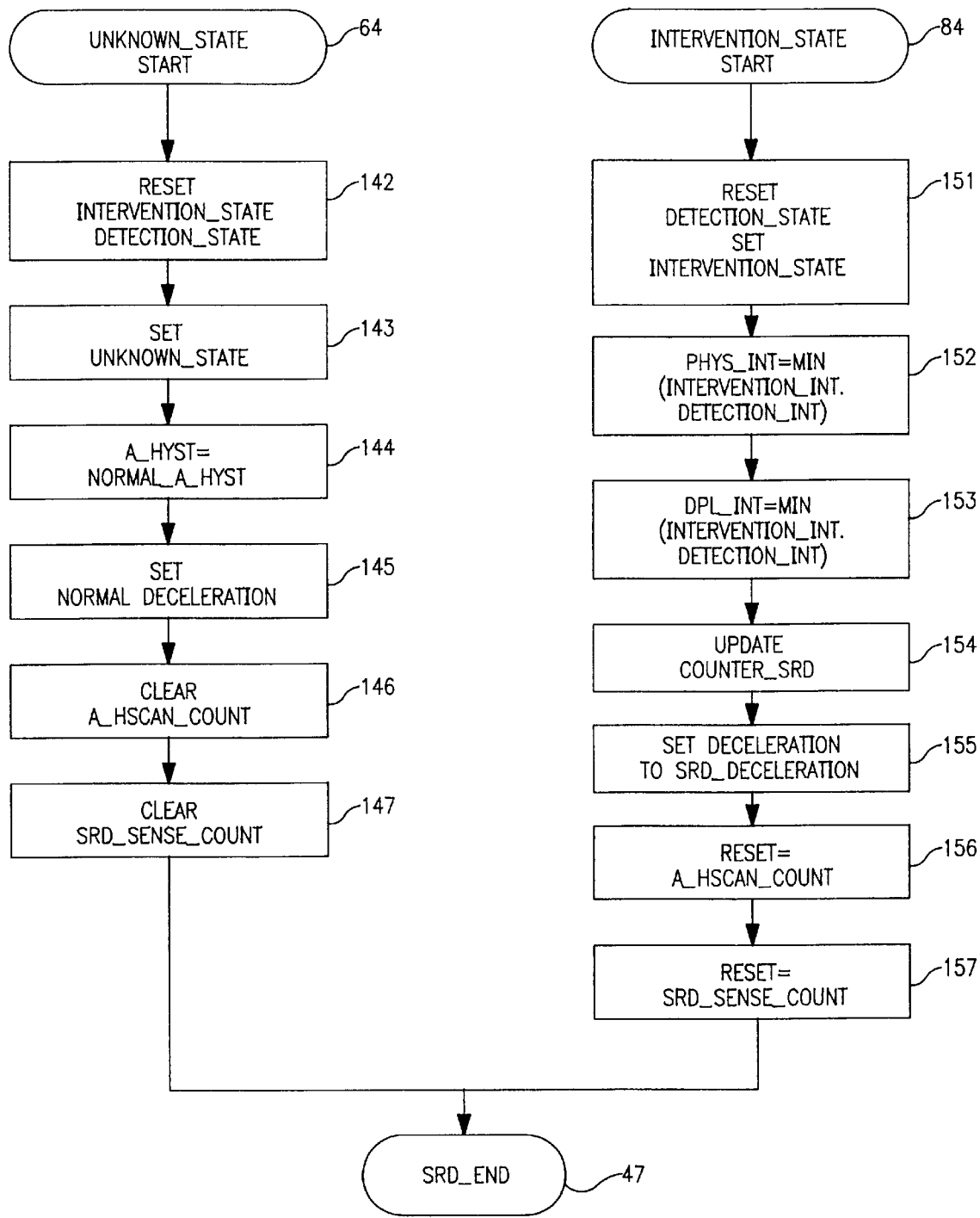
FIG. 7 is a flow diagram for starting the Intervention State and the Unknown State respectively.
Figure 8A:
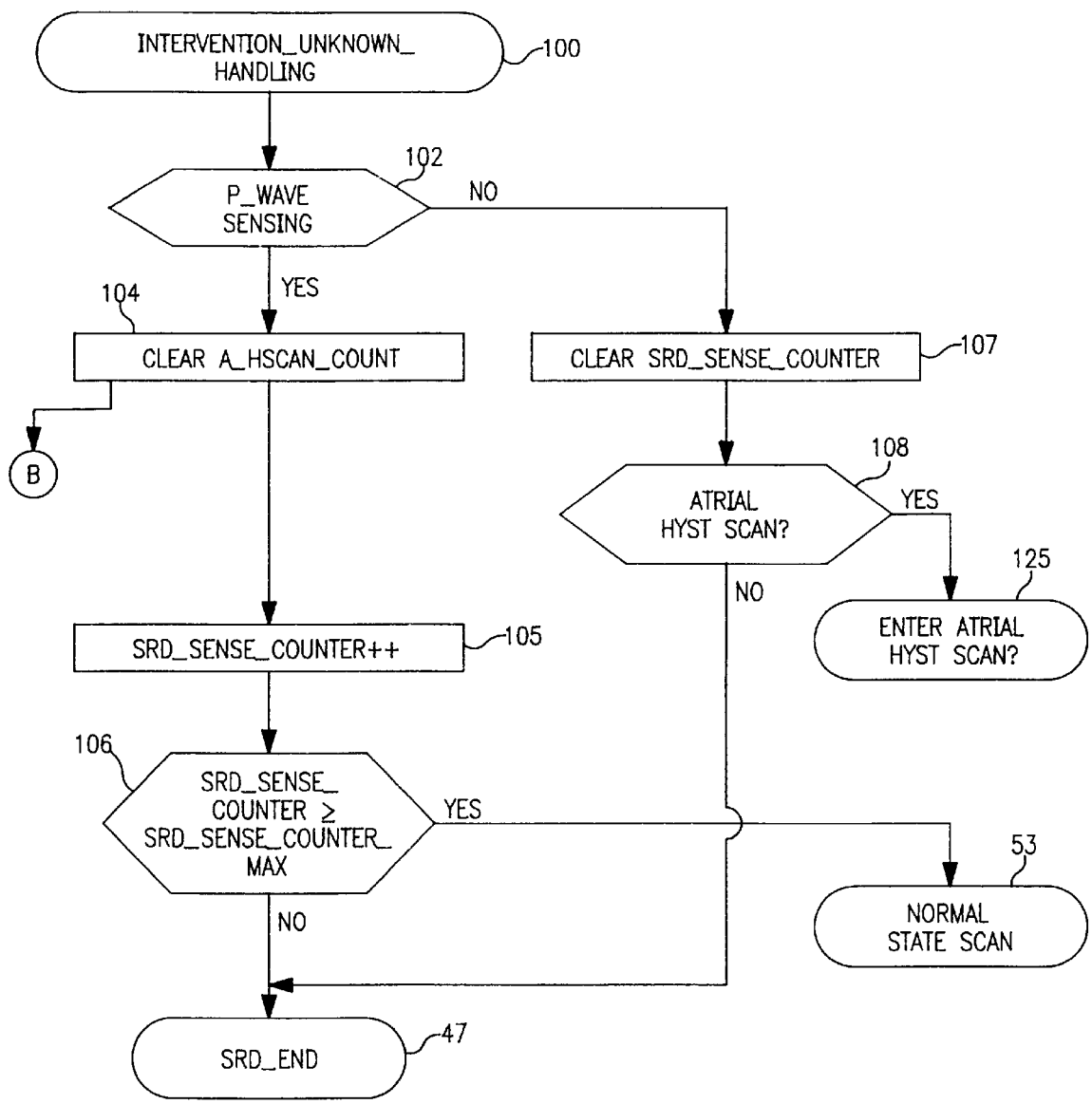
FIG. 8A is a flow diagram for handling when in either the Intervention State or the Unknown State in accordance with this invention, illustrating the cyclical steps taken as long as the pacemaker is in one of these states.
Figure 8B:
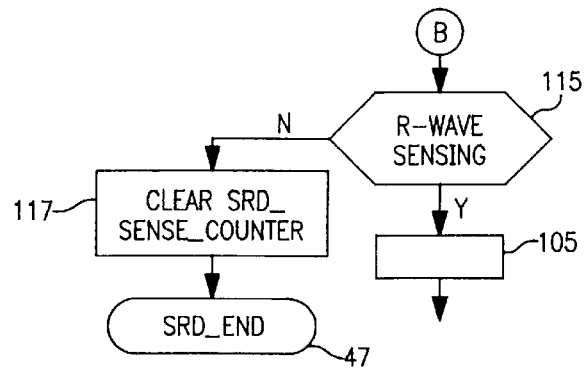
FIG. 8B shows a variation of the routine of FIG. 8A for DDI pacing.

Referring to FIG. 4(b), there is shown a flow diagram which provides an overview of the different states into which the SRD routine can place the pacemaker, which states are grouped within block 42; and how the SRD feature recognizes the states. Following execution of block 31, the pacemaker executes the SRD subroutine 33, shown here as blocks 37–40 and 42–49. At 37, the pacemaker checks to see if the SRD mode is programmed ON. If no, the routine branches to SRD_End, at 47. If yes, the routine proceeds to determine which of the states is presently set. As used in this discussion of FIG. 4(b), a determination that a state is "set" means either that the pacemaker is to go to the "start" portion for such state, or to the "Handling" portion, as is discussed in detail hereinbelow. At 38, it is determined if the Unknown_State is set. If yes, the routine goes to block 43, the Unknown_State routine, the Start portion of which is presented in detail in FIG. 7. Otherwise, at 39 it is determined if the Intervention_State has been set. If yes, the pacemaker goes to the Intervention_State routine 44 (the Start portion of the Intervention_State routine is shown in FIG. 7; the Intervention_Handling portion is shown in FIGS. 8A, 8B). If the answer at 39 is NO, the pacemaker goes to decision block 40, and determines if the Detection_State has been set, meaning that a sudden rate drop is suspected due to an AS-AP transition for a DDD pacemaker, or due to an AS-AP or VS-VP transition for a DDI pacemaker. If yes, the pacemaker goes to the Detection_State routine 45, shown in detail in FIG. 6. But if NO, then Normal State is logically concluded, and the pacemaker goes to the Normal_State routine 46, shown in detail in FIG. 5. The states have three possible ways to leave the SRD routine and return to the main flow, mainly by SRD_End 47; Atrial_Hyst_Scan_End 48, or Detect_End 49, as discussed below.

Figure 5:
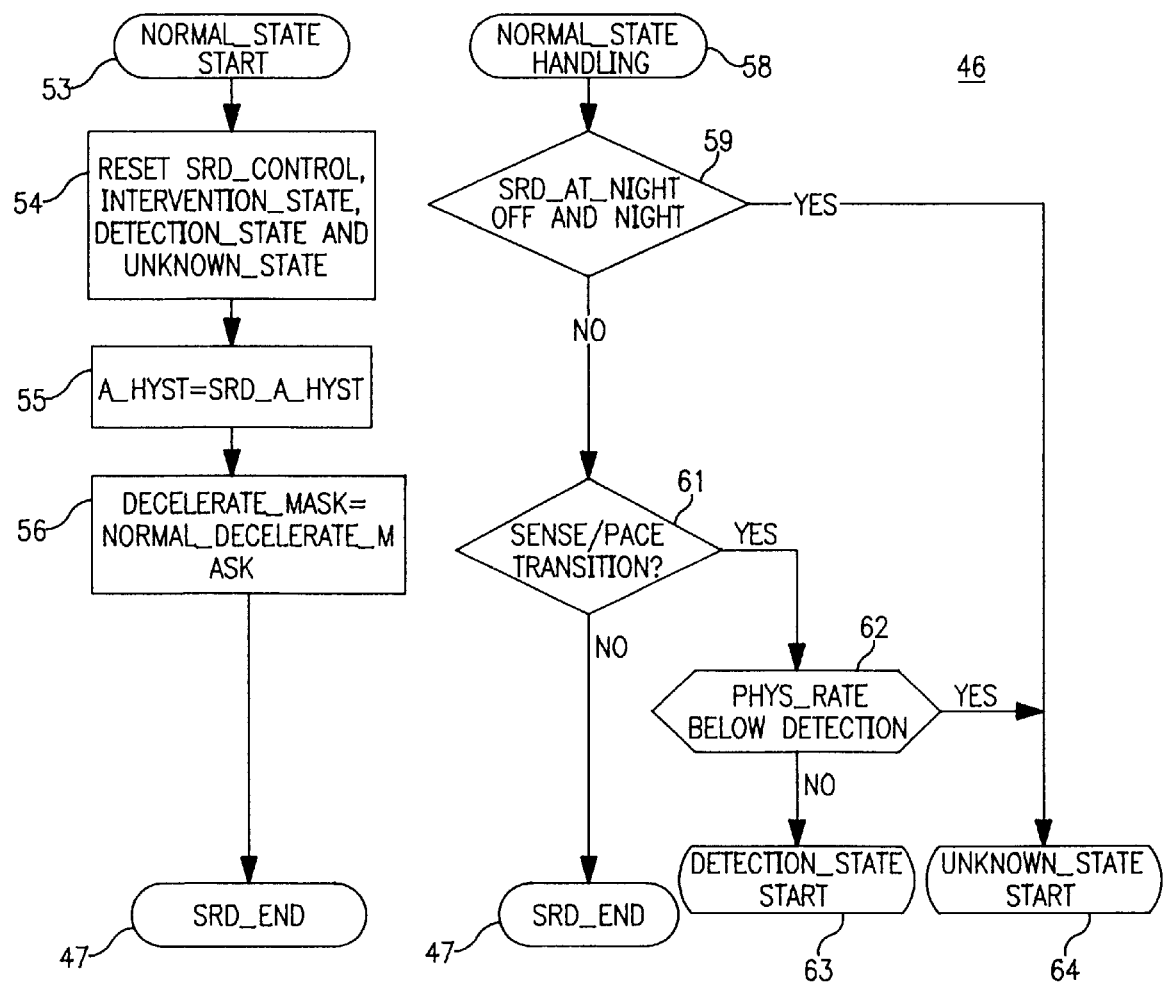
FIG. 5 is a flow diagram of a Normal State routine in accordance with this invention, showing when the pacemaker goes into the SRD Detection State.

Referring now to FIG. 5, there is shown a subroutine for starting the Normal State, and one for handling a cycle when in the Normal State. The Normal State is executed every cycle if the SRD is ON, no magnet is detected (in which case the pacemaker goes into the Unknown Situation state), and neither the Detection, Intervention or Unknown Situation state has been entered. Normal_State Start is entered from another state at 53. At 54, SRD control resets the other states. At 55, the atrial hysteresis, A_Hyst, is set equal to SRD_A_Hyst, which is a large hysteresis band set to prevent false detection of a sudden rate drop. At 56, the flywheel deceleration is set to a normal rate, and the routine exits at SRD_End 47. When in the Normal_State, Handling is entered cyclically at 58. At 59, the pacemaker checks to see if nighttime conditions indicate that SRD is OFF; is yes, since SRD cannot be detected, the routine branches to enter the Unknown_State Start routine at 64. Otherwise, the routine proceeds to 61, where it is determined whether there has been a sense/pace transition, in which case an SRD event is suspected. If no, the subroutine exits at 47. But if there has been a sense/pace transition in the atrium for a DDD pacemaker, or in the atrium or ventricle for a DDI pacemaker, the routine goes to block 62, and determines if Phys rate is below the Detection OFF rate. If yes, the situation is uncertain, as discussed in connection with FIG. 2(c), and the subroutine branches to 64 to start the Unknown_State. But if Phys rate is above the Detection OFF rate, then the pacemaker branches to start the Detection_State at 63.

Figure 6:
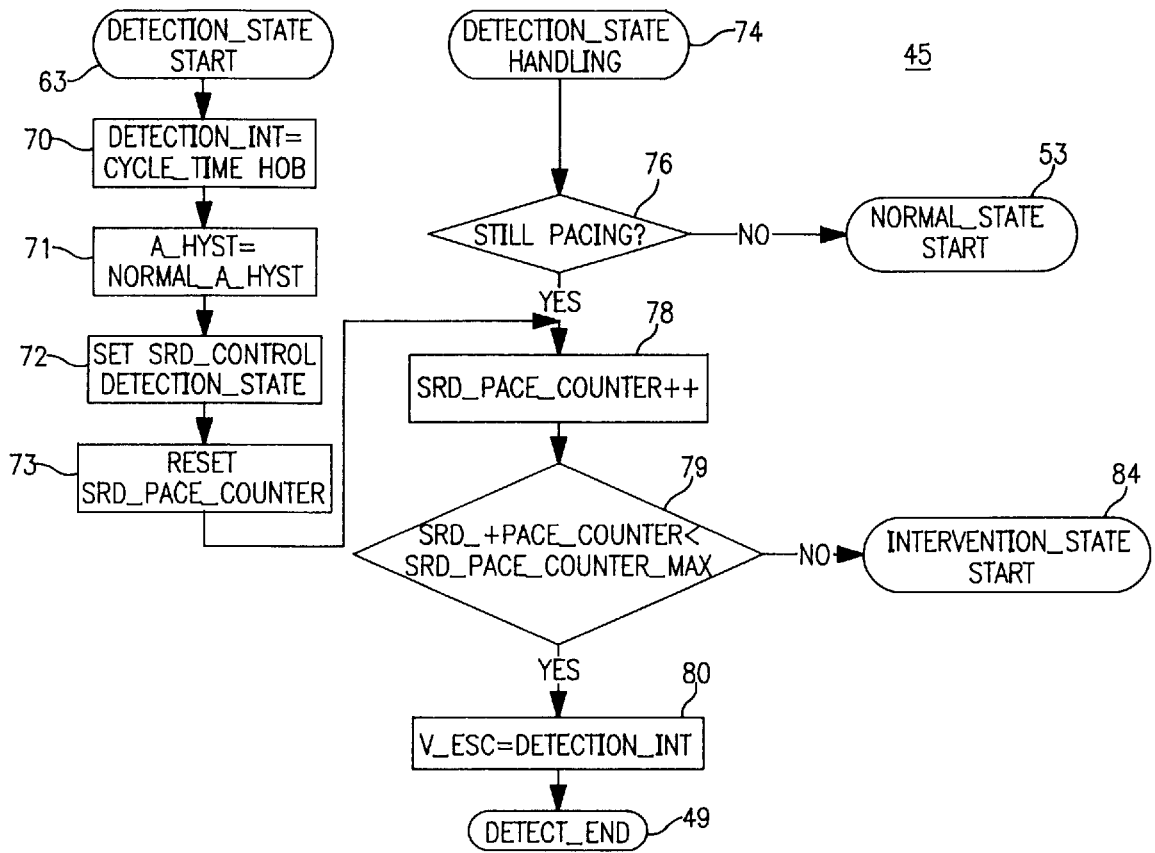
FIG. 6 is a flow diagram of a Detection State routine in accordance with this invention, illustrating the cyclical steps taken after there has been a sense/pace transition.

Referring now to FIG. 6, there is shown the Detection_State routine 45. If a transition has been detected during Normal_State handling, the pacemaker enters Detection_State Start at 63, and then at 70 the Detection_int is set, i.e., the interval at which pacing is done during the Detection State. This interval is set to correspond to the time duration of the last expired cycle that ended with an AP for DDD or DDI, or a VP for DDI. At 71, A_Hyst is set to Normal_A-Hyst, and at 72 SRD_Control is set to Detection_State, which means that the pacemaker will enter at block 74 during the next cycle. At 73, the SRD_Pace_Counter is reset to zero, to count paces delivered during the Detection State, and then the counter is incremented at 78. When Detection_State Handling is entered at 74, the pacemaker first determines whether pace pulses are still being delivered (76). If no, meaning that spontaneous atrial beats (DDD or DDI), or spontaneous ventricular beats (DDI) have reappeared, the routine goes to 53 to start the Normal_State. But if pacing continues, the SRD_Counter is incremented at 78. At 79, it is determined if the counter is still less than a programmable Max value, e.g., 1–5. If no, this means that SRD is confirmed, since no spontaneous rate reappeared above the Detection_int. Consequently, the pacemaker enters Intervention_State Start at 84. However, if Detection State pace counting is to continue, from 79 the routine goes to 80 and sets V_Esc to the Detection_Int. The routine goes back to the main flow through Detect_End block 49.

Referring now to FIG. 7, there are shown routines for starting the Unknown and Intervention states respectively. Each Start routine is used during one cycle for setting various counters and conditions; during following cycles the pacemaker proceeds directly to the Intervention_Unknown handling routine (shown in FIGS. 8A, 8B). The Unknown_State Start is entered at 64 when there has been an AS/AP transition in DDD or DDI or a VS/VP transition in DDI, and Phys_rate is below the Detection OFF rate, as discussed above. The routine also enters at 64 if a magnet has been applied, or the nighttime condition indicates that SRD is off. At 142 the bits which indicate Intervention State and Detection State are reset, and at 143 the bit representative of the Unknown_State is set, to indicate that the Unknown_State is active. At 144 atrial hysteresis is set to Normal_A_Hyst, and at 145 the deceleration is set to Normal_Deceleration, whereby the rate is allowed to step down once every $2^n$ cycles. At 146, the A_HScan_Count is cleared, or reset, to be ready to count paces for triggering an atrial hysteresis scan. At 147, the SRD_Sense_Counter is reset, to be ready to count normal senses in order to determine if the pacemaker can return to the Normal_State.

Intervention_State_Start is entered at 84, e.g., when SRD has been confirmed at block 79 (FIG. 6) of the detection routine. At 151, the Detection_State bit is reset, and the Intervention_State bit is set. At 152, Phys_int is set to the minimum of the programmed Intervention_Int or the Detection_int, usually the Intervention_int which corresponds to a higher rate. At 153, DPL_int is set to the same interval as Phys_int. At 154, the Counter_SRD is updated, whereby episodes of SRD are counted. At 155, the deceleration rate is set to SRD_Deceleration, which generally is slower for Intervention_State than the other states. At 156 the A_HScan_Count is reset, and at 157 the SRD_Sense_Count is reset. After either start routine, the pacemaker leaves through SRD_End to return to the main flow.

Referring now to FIG. 8A, there is shown a flow diagram of a routine in a DDD pacemaker for handling in the Intervention State, and also when the pacemaker is in the Unknown Situation state. Although the handling routine is the same for each, the pacing rates are somewhat different due to the different initial settings as discussed above. The Intervention_Unknown handling routine is entered at 100. At 102, it is determined whether the pacemaker is sensing in the atrium, i.e., has a spontaneous P-wave occurred? If yes, the routine goes to 104, and clears A HScan counter. Next, for a DDD pacemaker, 10 at 105 the SRD_Sense Counter is incremented. At 106 it is determined whether the Sense Counter count is greater than the programmable max value, e.g., 3. If no, the pacemaker is to stay in the Intervention State, and the routine exits. However, if yes, this means that the reappearance of a natural rate is confirmed, and intervention is to be ended. The routine then goes to 53 to start the Normal State.

Returning to block 102, if there is no P-wave sensing, at 107 the SRD Sense counter is cleared, as return to normal is confirmed only by n consecutive senses. At 108 it is determined whether the atrial scan feature is programmed. If no, the routine exits back to the main flow through 47. But, if Atrial Hyst Scan is programmed, the pacemaker enters the Atrial Hyst Scan routine (110, shown in FIG. 9) at 125.

The routine of FIG. 8A is altered for a DDI pacemaker, as illustrated in FIG. 8B. After performing the step of block 104, the routine goes to 115 and determines whether there has been R wave sensing, i.e., has there been a VS? If yes, there is no difference from the DDD case, and the routine proceeds to block 105. But if no, the SRD_Sense_Counter is cleared at 1I17, such that sense counting starts over, thereby extending the intervention state.

Figure 9:
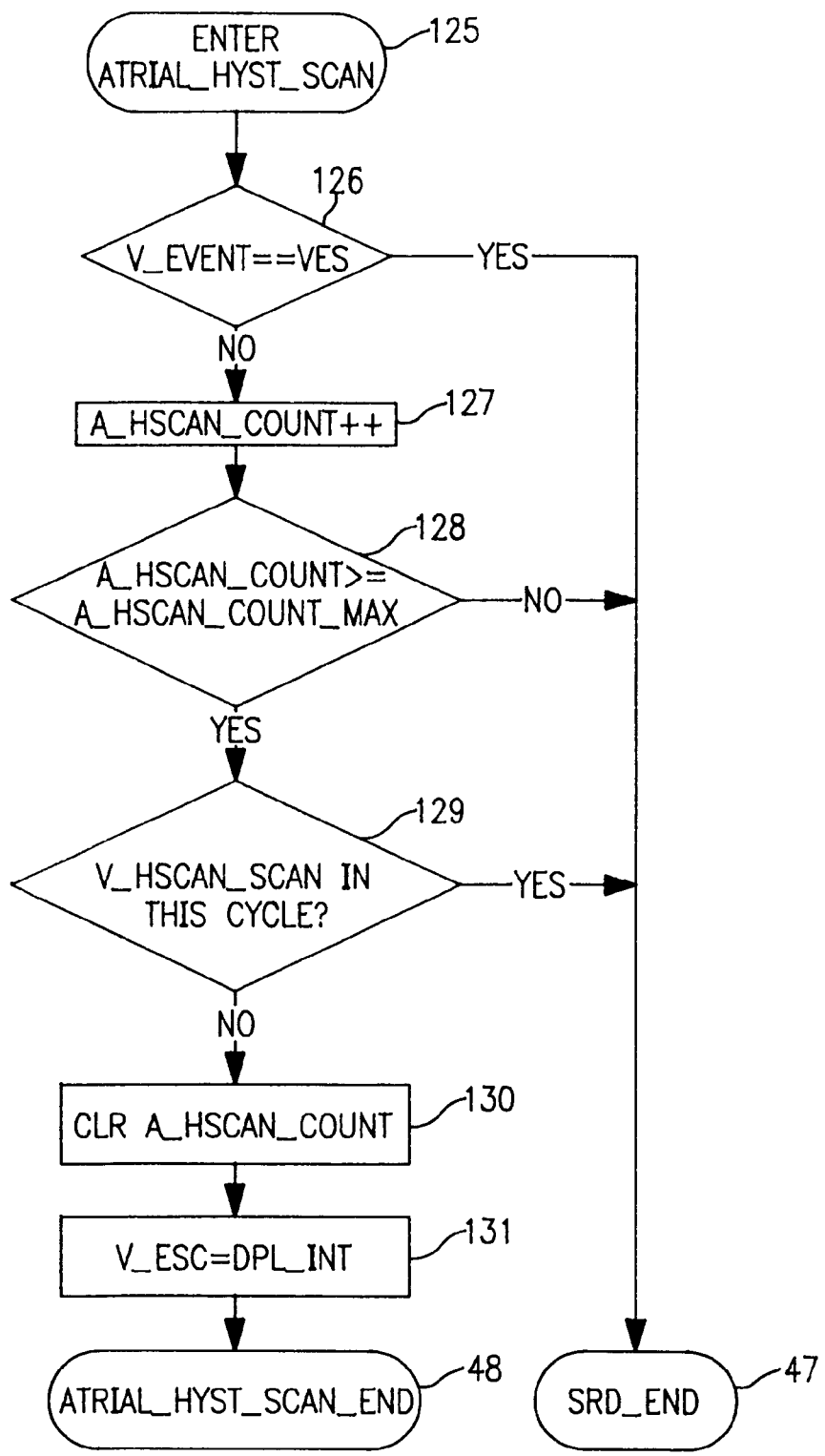
FIG. 9 is a flow diagram illustrating the atrial hysteresis scan which is part of the intervention routine in a preferred embodiment of this invention.

Referring to FIG. 9, at 126 it is determined whether the last ventricular event has been a Ventricular Extra Systole (VES). The counting of paces is frozen in case of a VES, so if one has occurred the pacemaker returns to the main flow through 47. Otherwise, the A_HScan_Count is incremented at 127, and at 128 the count is compared to the programmable Max count value. If the count is not equal to or greater than Max, the routine exits; but if it is, then it proceeds to 129 and determines whether there is a ventricular hysteresis scan during this cycle. Since an atrial hysteresis scan is not permitted during the same cycle as a ventricular hysteresis scan, the routine exits if there is a ventricular hysteresis scan. But, if not, then at 130 the A_HScan_Count is cleared, and at 131 the ventricular escape interval is set to DPL_int.

There has thus been disclosed a pacemaker system for detecting SRD, which distinguishes between a pathological and a physiological rate drop. The detection of SRD is achieved by simply determining when there has been a sense/pace transition, and the spontaneous rate is not recovered for a predetermined number of cycles. This reliable detection scheme is enabled by using a large dynamic hysteresis detection band, and by utilizing a detection OFF rate for discriminating physiological bradycardia from SRD.

We claim:

1. A dual chamber pacing system for pacing a patient, having a pacemaker and lead means for delivering pacing pulses from said pacemaker to the patient's heart and for delivering sensed spontaneous heartbeat signals from said patient's heart to said pacemaker, said pacemaker comprising:

pacing means for generating pacing pulses upon time out of an escape interval without an intervening spontaneous beat;

atrial rate means for determining the patient's atrial rate when spontaneous atrial beats are occurring;

hysteresis means for determining a dynamic atrial hysteresis rate which tracks said atrial rate through a rate range limited by a lower rate limit, and escape means for setting said escape interval corresponding to said atrial hysteresis rate;

transition means for determining a transition when a pace pulse is delivered to one of the patient's heart chambers following a cycle where a spontaneous beat was sensed in such chamber;

and SRD means for detecting if said transition represents a physiological bradycardia or a sudden rate drop.

2. The system as described in claim 1, wherein said pacemaker is a DDD pacemaker, and said transition means comprises means for determining a transition from an atrial sense to an atrial pace, and wherein said SRD means comprises means for detecting sudden rate drop only following a said transition from atrial sense to atrial pace.

3. The system as described in claim 1, wherein said pacemaker is a DDI pacemaker, and said transition means comprises means for determining a transition from an atrial sense to an atrial pace and a transition from a ventricular sense to a ventricular pace, and wherein said SRD means comprises means for detecting sudden rate drop following either of said transitions.

4. The system as described in claim 1, wherein said SRD means comprises means for storing a detection off rate, and means for determining whether said spontaneous rate was below said detection off rate just before a said transition.

5. The system as described in claim 4, wherein said hysteresis means comprises band means for storing a hysteresis band value, and clamp means for clamping said hysteresis rate at a rate at said band value below said detection off rate.

6. The system as described in claim 1, comprising response means for controlling generation of atrial pacing pulses in response to a said detection of sudden rate drop.

7. The system as described in claim 6, wherein said response means comprises intervention rate means for controlling generation of atrial pacing pulses at a variable intervention rate following detection of sudden rate drop.

8. The system as described in claim 7, wherein said response means comprises hysteresis scan means for periodically extending the atrial escape interval to correspond to a rate which is below said intervention rate.

9. The system as described in claim 1, wherein said SRD means comprises means for maintaining the atrial escape interval at a detection interval corresponding to the hysteresis rate when a said transition occurred, and detection pacing means for pacing said patient at a detection rate corresponding to said detection interval for a programmable number of cycles.

10. The system as described in claim 9, wherein said detection pacing means comprises means for pacing at said detection rate for 1–5 cycles.

11. A dual chamber pacing system for pacing a patient, having a pacemaker and lead means for delivering pacing pulses from said pacemaker to the patient's heart and for delivering sensed heartbeat signals from said patient's heart to said pacemaker, said pacemaker comprising:

atrial pace means for generating atrial pace pulses for delivery to said patient's atrium;

atrial sense means for detecting atrial senses representative of natural atrial beats, and atrial rate means for determining the atrial rate of natural atrial beats from said atrial senses;

hysteresis means operative while atrial senses are detected for determining a hysteresis rate at a programmable hysteresis band below said atrial rate while natural atrial beats are sensed;

atrial hysteresis pacing means for controlling said atrial pace means to generate an atrial pace pulse at a hysteresis escape interval corresponding to said hysteresis rate when no atrial sense is determined before time out of said hysteresis escape interval, and for continuing to generate atrial pace pulses at said hysteresis rate in the absence of a detected atrial sense for a programmable $n_1$, cycles;

detection means for detecting sudden rate drop (SRD) when no atrial beat is sensed at a rate above said atrial hysteresis rate for said n, cycles at said atrial hysteresis rate; and intervention means for controlling said atrial pace means to generate atrial pace pulses in accord with a predetermined intervention routine following a detection of SRD.

12. The system as described in claim 11, comprising programmable means for setting $n_1$ to a number within the range of 1–5.

13. The system as described in claim 11, comprising means for storing a detection off rate, means for determining when said atrial rate is below said detection off rate, and enabling means for enabling said detection means to detect SRD only when said atrial rate is above said detection off rate just before said atrial rate drops below said atrial hysteresis rate.

14. The system as described in claim 11, wherein said intervention means comprises means for intervention pacing at a programmable intervention rate for at least one cycle following detection of SRD in the absence of a natural beat at a rate above said intervention rate.

15. The system as described in claim 14, wherein said intervention means comprises intervention hysteresis means for pacing at an intervention hysteresis rate for at least one cycle every $n_2$ paced beats during intervention pacing.

16. The system as described in claim 14, wherein said intervention means comprises flywheel means for decreasing pacing rate from said intervention rate at a programmable rate of rate decrease.

17. The system as described in claim 11, wherein said pacemaker is a DDD pacemaker, and wherein said detection means comprises AS/AP means for determining when an atrial pulse follows a sensed natural atrial sense.

18. The system as described in claim 11, wherein said pacemaker is a DDI pacemaker, and wherein said detection means comprises means for determining when a cycle having an AS and a VS is followed by a cycle having an AP or a VP.

19. The system as described in claim 11, wherein said atrial rate means has limit means for determining a rate range above a programmable lower limit, and wherein said hysteresis means has band means for determining said hysteresis rate corresponding to a substantially constant number of ms below said atrial rate measure throughout said rate range.

20. A dual chamber pacemaker system for pacing a patient, comprising hysteresis means for establishing a dynamic hysteresis rate that tracks below the patient's spontaneous atrial rate, means for delivering an atrial pace pulse after time out of an escape interval corresponding to said dynamic hysteresis rate in the absence of a sensed atrial beat, and SRD detection means for detecting SRD when an atrial sense is followed by an atrial pace pulse and pacing continues for a predetermined number of cycles at said dynamic hysteresis rate.

21. The system as described in claim 20, wherein said hysteresis means continuously establishes said hysteresis rate corresponding to a predetermined number of ms below the current rate of spontaneous atrial beats as long as spontaneous atrial beats are sensed.

22. The system as described in claim 20, comprising intervention means for controlling pacing in accord with an intervention subroutine following a said SRD detection.

\* \* \* \* \*